United States Patent [19]

Shiraishi et al.

[11] Patent Number: 4,865,967
[45] Date of Patent: Sep. 12, 1989

[54] AUTORADIOGRAPHIC GENE-SCREENING METHOD

[75] Inventors: Hisashi Shiraishi, Minami-Ashigara; Junji Miyahara; Hisatoyo Kato, both of Kaisei, all of Japan

[73] Assignee: Fuji Photo Film Co., Ltd., Kanagawa, Japan

[21] Appl. No.: 127,605

[22] Filed: Nov. 30, 1987

Related U.S. Application Data

[63] Continuation of Ser. No. 624,813, Jun. 26, 1984, abandoned.

[30] Foreign Application Priority Data

Jun. 29, 1983 [JP] Japan .................................. 58-119410

[51] Int. Cl.$^4$ ...................... C12Q 1/68; G01N 33/566
[52] U.S. Cl. ......................................... 435/6; 436/501; 935/78
[58] Field of Search ............... 435/6; 935/78; 436/501

[56] References Cited

U.S. PATENT DOCUMENTS

| | | | |
|---|---|---|---|
| 4,239,968 | 12/1980 | Kotera et al. | 250/327.5 |
| 4,297,587 | 10/1981 | Buchanan et al. | 250/483.1 |
| 4,302,671 | 11/1981 | Kato et al. | 250/327.5 |
| 4,389,670 | 6/1983 | Davidson et al. | 250/363 R |

FOREIGN PATENT DOCUMENTS 0056638  7/1982  European Pat. Off.

OTHER PUBLICATIONS

Grunstein et al. (1975), Proc. Nat'l Acad. Sci., 72:3961-3965.
Hanahan et al. (1980), Gene 10:63-67.
Benton et al. (1977), Science 196:180-182.

*Primary Examiner*—Barry S. Richman
*Assistant Examiner*—Jill Johnston
*Attorney, Agent, or Firm*—Gerald J. Ferguson, Jr.

[57] ABSTRACT

An autoradiographic gene-screening method employing a hybridization process, which comprises:
(1) a step of transferring a portion of genetic clones cultured on a culture medium onto a filter to fix them thereonto;
(2) a step of hybridizing the genes of said clones fixed onto said filter with radioactively labeled probes;
(3) a step of obtaining two dimensional information on the location of the radioactively labeled substances on the filter which comprises placing said filter having been subjected to the hybridization and a stimulable phosphor sheet in layers for a given period of time to cause said stimulable phosphor sheet to absorb at least a portion of radiation energy emitted by the radioactively labeled substances on the filter, exciting said sheet with an electromagnetic wave to release the radiation energy stored in said sheet as stimulated emission, and detecting the stimulated emission to obtain a locational information on the radioactively labeled substances on the filter; and
(4) a step recovering the clones on the culture medium according to the obtained locational information.

8 Claims, 2 Drawing Sheets

AUTORADIOGRAPHIC GENE-SCREENING METHOD

This application is a continuation of Ser. No. 624,813, filed 6/26/84, now abandoned.

BACKGROUND OF THE INVENTION

1. Field of the Invention

This invention relates to an autoradiographic gene-screening method.

2. Description of Prior Arts

In molecular biology which has been rapidly developed in recent years, it is essential to obtain genetic information on organisms so as to make the function of the organisms or the mechanism of replication clear. For such purpose, it is required to screen genes having the specific genetic information out of the whole genomes and to obtain a large amount of said selected genes. This process is termed "cloning of genes".

Recently, the cloning of genes has been paid much attention in industry, since it makes it possible to increase the production efficiency of useful products including pharmaceuticals such as interferons, foods such as protein, drought-resistant crops, chemical products, etc.

However, the cloning of genes is difficultly performed in the industry, because the ratio of the objective gene to the whole genomes is very low so that the screening of the specific gene is very difficult. Thus, success or failure of the cloning of genes depends upon whether the screening of genes can be efficiently carried out or not. Further, said screening is carried out as an important means for identifying corresponding genes in the genetic diagnosis of hereditary diseases.

As methods for screening genes, various attempts have been made. As typical methods, there can be mentioned: a method which comprises a process of isolating or purifying the objective gene by a chemical analysis procedure such as column chromatography or electrophoresis utilizing the difference of molecular weights, chemical characteristics, etc. of the gene; a biological method which comprises screening the objective gene by utilizing the difference of manifestation character against drug resistance, enzyme activity. etc.; and a probe method which utilizes the ability to form a hybrid between complementary DNAs or RNAs (that is called "hybridization method").

Among these screening methods, the chemical analysis method is hardly employed in practice, since the amount of gene is very small and further the proportion of the objective gene to whole genomes is very small so that it is very difficult to selectively separate the objective gene. The biological method has a disadvantage in that manifestation of function related to the objective gene is indispensable to the method and not always active. As compared with these two methods, the probe method has advantages in that hybridization occurs very selectively and that the procedure is very simple.

For example, the typical gene-screening method utilizing colony hybridization process is carried out in the following manner.

In the first place, a recombinant DNA including a DNA fragment having the objective gene is prepared. In more detail, a plasmid obtained from *Escherichia coli* which is to serve as a vector is cleaved by a specific restriction enzyme. A DNA or DNA fragment containing the objective gene is also cleaved by the same restriction enzyme so that both the plasmid vector and the DNA have the same cohesive end. Both are then joined to each other at the corresponding ends using DNA ligase, whereby the recombinant plasmid is obtained.

The DNA fragment containing the objective gene can be also obtained, for example, by randomly cleaving a DNA containing the objective gene by a shotgun method and appropriately restoring the end of each of the resulting DNA fragments using DNA polymerase.

In the second place, *E. coli* is infected with the so-obtained recombinant plasmid and planted on an agar plate culture medium in a dispersed state to form colonies (clones having the same gene produced by proliferation of *E. coli* ). The agar plate culture medium on which colonies are formed, is hereinafter referred to as master plate.

In the third place, a part of the colonies is transferred onto a fresh filter, for example, by a replica plating method, etc. The resulting filter is hereinafter referred to as replica filter. This replica filter is placed on a fresh agar plate culture medium and incubated until the colonies are grown to an appropriate size. The filter is then peeled off from the agar plate medium and hybridization is carried out thereon.

The hybridization is carried out in the following manner. The cells of *E. coli* on the filter are lysed and the resulting exposed plasmid DNA is denatured to form a single-stranded DNA which is then fixed on the filter. Separately, DNA or RNA which is complementary to DNA containing the objective gene is radioactively labeled to prepare a probe.

In the fourth place, the radioactively labeled DNA or RNA is then hybridized with the denatured DNA on the filter. Thus, only a hybrid of a DNA containing the objective gene with the radioactively labeled DNA or RNA is formed on the filter and it is at the same time radioactively labeled. The hybridized filter is then subjected to autoradiography, whereby the colonies containing the objective gene are identified and the so identified colonies are collected from the master plate which has been stored at a low temperature.

Accordingly, through the above-described gene-screening procedure (hybridization utilizing) of recombinant genes, the objective gene clones are obtained.

As other methods for screening genes utilizing hybridization, there can be mentioned a screening method utilizing plaque hybridization.

In the plaque hybridization method, phage (virus which invades bacteria through infection and lyses their cells, resulting in growth of the virus) is used as a vector, and a replica of plaque formed on the master plate containing bacteria serving as a host is formed on a filter. Subsequently, a hybrid with a radioactively labeled probe is formed on the filter in a similar manner to that described above.

The above-summerized gene-screening methods utilizing colony hybridization or plaque hybridization are described in more detail in the following literatures.

METHODS IN ENZYMOLOGY, Vol. 68, pp. 379–395 (edited by Ray Wu, ACADEMIC PRESS, NEW YORK, 1979)

PROTEIN, NUCLEIC ACID & ENZYME (in Japanese), Vol. 26, No. 4, pp. 575–583 (1981).

In the conventional autoradiography employed for the gene-screening, a radiographic film such as a high sensitivity radiographic film is combined in layers with a filter retaining a captured radioactively labeled probe for a given time so that the film is exposed to the radiation. A radiographic intensifying screen is generally employed to enhance the detection sensitivity of autoradiography. Such autoradiography is described, for example, in the following literature: Method in Biochemical Experiment, Vol. 6, Method in Tracer Experiment I, pp. 271-280, "B. Autoradiography" by Toru Sueyoshi & Akiyo Shigematsu (Tokyo Kagaku Dozin Ltd., 1977).

Therefore, the autoradiography is an important means for identifying the objective gene and obtaining two dimensional information on the location of said gene in the gene-screening method. Further, it can be said that the autoradiography is a very useful means, since the isolation and purification of the objective gene can be done according to the obtained locational information. Nevertheless, such useful autoradiography is not free from several drawbacks in the practical use when applied to the gene-screening method utilizing the hybridization mentioned above.

As described above, in the conventional autoradiography, a filter containing a radioactively labeled substance is brought into contact in layers with a radiographic film such as a high-sensitivity radiographic film for a given time so that the film is exposed to the radiation and then a visible image indicating the position of the radioactive substances is obtained.

The primary drawback resides in that the exposure operation requires a long period of time. The exposure operation in the conventional autoradiographic screening is usually carried out for several days, and requires at least several tens of hours even when a radiographic intensifying screen is used. This is because the amount of DNA fixed on the filter is small and the radioactively labeled substance (radioactively labeled probe) is a DNA and RNA partially labeled generally with $^{32}P$ so that intense radioactivity is not imparted thereto.

The second drawback resides in that the exposure operation should be carried out usually at a low temperature, for example, a temperature in the range of 0° C. to $-0°$ C. This is because a latent image on silver salt which is formed by exposure to a radiation or fluorescence on the film tends to fade at a relatively high temperature such as room temperature and the so degraded latent image can be no longer developed to give a readable image. Further, the silver salt is easily fogged chemically through migration of deleterious ingredients from the hybridization-processed filter to the silver salt layer at such a high temperature. Another reason resides in that the silver salt difficultly forms a latent image at a relatively high temperature such as room temperature in the case of utilizing an intensifying screen which gives an emission of low intensity.

The third drawback resides in that the exposure ought to be carried out in a dry state to prevent the radiographic film from wetting and being fogged. Usually, this is done after the filter is dried, othewise enclosed with a synthetic resin wrapping film, etc.

When the image obtained by the autoradiography is fogged as described above, the hybridized DNA is hardly distinguished on the obtained image and hence, the result of screening is made remarkably unfavorable.

For these reasons, the operation involved in the conventional autoradiography is complicated, whereby the gene-screening procedure is made complicated as a whole.

Other drawbacks of the conventional autoradiographic gene-screening method are given below.

The photosensitive silver salt of the radiographic film is readily influenced by physical irritation and the radiographic film easily produces fogging under application of physical pressure caused by the contact of the film with the hands of operators or the instrument in the exposure operation. Such unfavorable phenomena also cause lowering in accuracy of the gene-screening. In order to avoid the occurrence of physical fogging of the radiographic film, much skill and caution must be taken in the handling of the film, and hence, the screening operation is further complicated.

The exposure operation in the conventional autoradiographic gene-screening method is conducted over a long period of time as described above, so that it is unavoidable that the radiations of natural origin and radioactive impurities incorporated in the filter in addition to the radioactively labeled substance take part in the exposure of the radiographic film. Thus, the accuracy of the resulting information on the location of the objective radioactively labeled substance is lowered. In order to eliminate such interference and to set appropriate exposure conditions, parallel experiments using control samples are generally carried out to find out exposure time, but such experiments have disadvantages in that the number of the experiments is increased because of involving such parallel experiments and preliminary experiments for ascertaining appropriate exposure time and hence, the operation is made complicated and less economical as a whole.

The operation of collecting the objective gene is performed in such a manner that the master plate is alligned with the autoradiograph to allow the clone (colonies and plaques) corresponding to positive-signals indicating the presence of the radioactively labeled substances to be picked up. Therefore, if the formation of clones on the culture medium is insufficient, the hybridization is insufficient, or the condition for preparing the replica filter or for exposure of the filter is improper, the accuracy of the gene-screening is lowered. Otherwise, the screening becomes impossible in some cases and accordingly the number of the screening operation involved necessarily increases.

SUMMARY OF THE INVENTION

The present inventors have made studies to eliminate the aforementioned disadvantageous features associated with the conventional autoradiographic gene-screening method, and discovered that by using a stimulable phosphor sheet having a phosphor layer containing a stimulable phosphor as a radiosensitive material in place of the radiographic film, the aforementioned disadvantages can be effectively eliminated or reduced.

Accordingly, the present invention provides an autoradiographic gene-screening method employing a hybridization process, which comprises:

(1) a step of transferring a portion of genetic clones cultured on a culture medium onto a filter to fix them thereonto;

(2) a step of hybridizing the genes of said clones fixed onto said filter with radioactively labeled probes;

(3) a step of obtaining two dimensional information on the location of the radioactively labeled substances on the filter which comprises placing said filter having been subjected to the hybridization and a stimulable phosphor sheet containing a stimulable phosphor in layers for a given period of time to cause said stimulable phosphor sheet to absorb at least a portion of radiation energy emitted by the radioactively labeled substances on the filter, exciting said sheet with an electromagnetic wave to release the radiation energy stored in said sheet as stimulated emission, and detecting the stimulated emission to obtain a locational information on the radioactively labeled substances on the filter; and (4) a step of recovering the clones on the culture medium according to the obtained locational information.

The two dimensional "information on location" of the radioactively labeled substance on the filter in the present invention refers to various information typically such as the location of the radioactively labeled substance or its aggregate on the filter, for example, information on the location and the shape of the aggregate of the radioactively labeled substances on the filter and on the concentration, the distribution, etc. of said radioactively labeled substance or its aggregate. Such information can be obtained singly or in combination.

BRIEF DESCRIPTION OF DRAWINGS

FIG. 1 is a flow chart illustrating the gene-screening method of the present invention wherein:

(a) shows a master plate having colonies formed thereon in which 1a means colony, 2a means culture medium and 3a means mark given with a drawing ink;

(b) shows a replica filter in which 1b means colony, 2b means filter and 3b means mark given with a drawing ink;

(c) shows a filter having hybrids formed thereon in which 1c means hybridized colony, 2c means filter, 3c means mark given with the drawing ink as well as with a radiographic ink and 4c means unhybridized colony; and (d) shows a visualized autoradiograph wherein 1d means black spot, 2d means radiographic film and 3d means black spot which is formed through exposure to radiation from the radiographic ink.

DETAILED DESCRIPTION OF THE INVENTION

The stimulable phosphor sheet used in the present invention is also called a radiation image storage panel and disclosed in, for example, U.S. Pat. No. 4,239,968 etc., and thus its general constitution is already known.

The stimulable phosphor sheet comprises a stimulable phosphor in which said stimulable phosphor is capable of absorbing radiation energy having passed through an object or emitted by an object; and releasing the radiation energy stored in said stimulable phosphor of said sheet as fluorescense when said sheet is excited with an electromagnetic wave (stimulating rays) such as visible or infrared rays. The fluorescense is photoelectrically detected and converted into an electric signal which is then reproduced as a visible image on a display device such as CRT or represented as a locational information in the form of symbols and/or numerals. The stimulable phosphor sheet can be used repeatedly after erasing the radiation energy remaining therein which is done after being subjected to the read-out procedure. Therefore, the use of the stimulable phosphor sheet in the autoradiographic process according to the present invention is very advantageous.

According to the present invention, the stimulable phosphor sheet containing a stimulable phosphor is used in place of the radiographic film or a combination of the film with a radiographic intensifying screen used in the conventional autoradiographic gene-screening method for obtaining two dimensional information on the location of the radioactively labeled substance fixed on a filter. By the use of the stimulable phosphor sheet, not only the exposure time is greatly shortened, but also the accuracy of the resulting information on the location of radioactively labeled substance does not lower even when the exposure is carried out at an ambient temperature or at a temperature around ambient temperature. Therefore, the exposure operation previously involving many hours under chilling, is made simple and hence, the autoradiographic operation for obtaining two dimensional information on the location of the radioactively labeled substance is greatly simplified.

Moreover, the exposure time in the autoradiography is greatly shortened so that time required for one screening operation can be shortened.

Generally, the operation for screening the objective gene is carried out two or more times. For example, one human DNA contains genetic information being expressed by a length of totally about $10^9$ bases (here "base" means a nucleotide) and one genetic information (i.e., information attached to single gene) is generally expressed by a length of about $10^3$ bases. Accordingly, in the case that the human DNA is screened, at least $10^6$ DNA fragments have to be screened to collect a certain specified gene. Even though $10^4$ fragments can be screened on one filter (about 15 cm in diameter) in one operation by the plaque hybridization method, at least one hundred filter sheets must be treated as a whole. Therefore, it is practically very advantageous that one screening operation can be efficiently conducted in a short time.

It is not desirable for organisms that the master plate from which colonies or plaques are collected is preserved over a long period of time. Thus, it is also very advantageous that the operation can be carried out in a short time.

When the stimulable phosphor sheet is used as a radiosensitive material, there is not always required visualization for obtaining two dimensional information on the location of the radioactively labeled substance which is stored onto the phosphor sheet and it is possible to obtain the locational information in any forms of an image, symbols and/or numerical values and a combination thereof by scanning the stimulable phosphor sheet with an electromagnetic wave such as a laser and reading out the locational information on the radioactively labeled substance. Further, it is also possible to obtain a desired information in the desired forms by further processing the above-described information with an appropriate electric means.

This means that it is possible that the operation for collecting clones containing the objective gene according to the resulting information on the location of the radioactively labeled substance is made easy and hence, the accuracy of screening is enhanced and its efficiency is improved.

Further, when the stimulable phosphor sheet is used as the radiosensitive material in autoradiography, there occurs no problem of chemical and physical fog which is a nuisance in the case of using the conventional radiographic film. Hence, the use of the stimulable phosphor sheet is very advantageous from the viewpoints of an improvement in the accuracy of screening and workability. Further, it is also possible to readily eliminate or reduce the disadvantageous features associated with the conventional operation such as lowering in the accuracy caused by natural radioactivity or radioactivity of the impurities contained in the filter, through electrically processing the locational information stored in the stimulable phosphor sheet.

The following illustrates the gene-screening method utilizing colony hybridization as an embodiment of the autoradiographic gene-screening method of the present invention.

Figure 1:
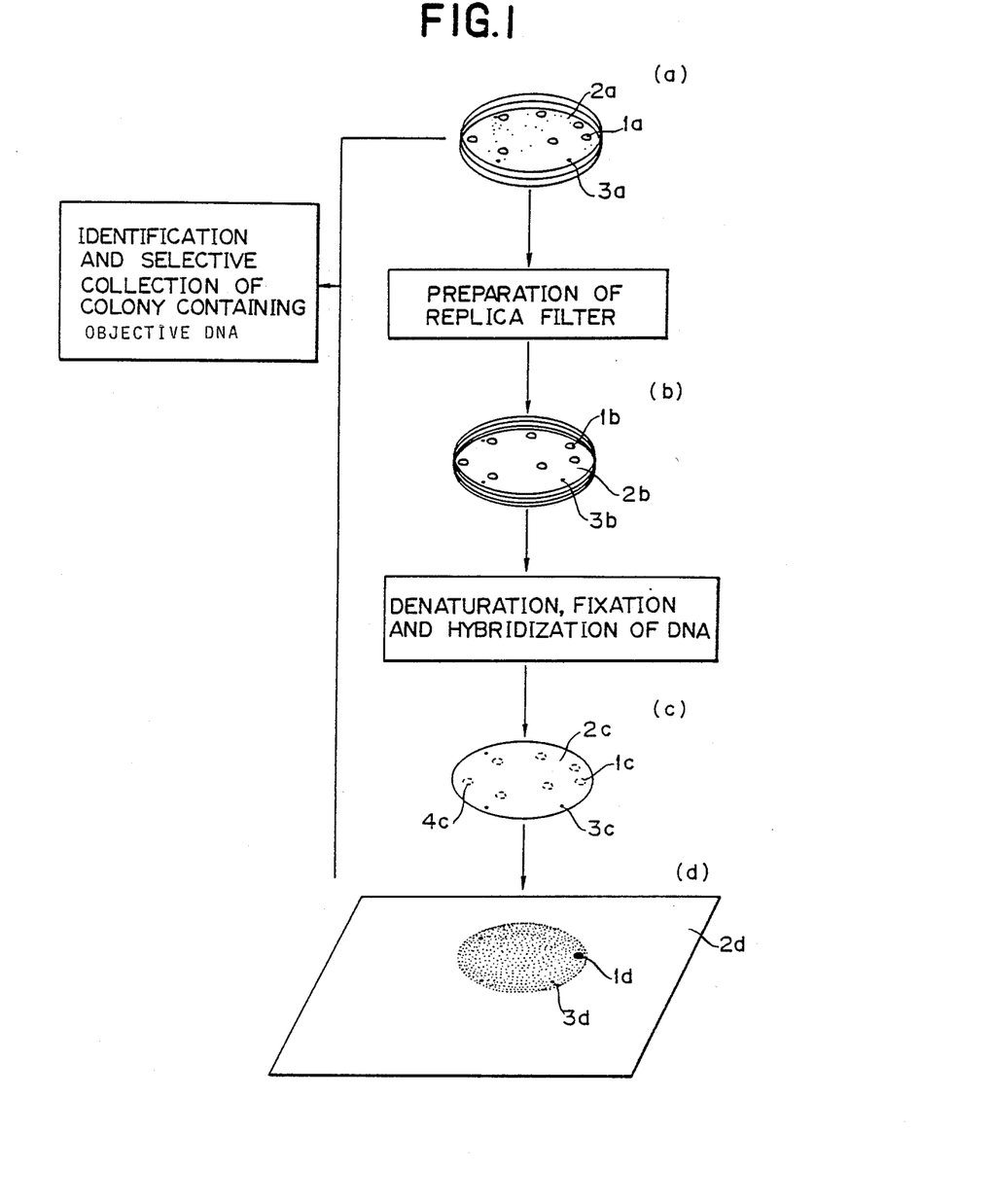

FIG. 1 schematically illustrates an embodiment of the gene-screening method utilizing hybridization according to the present invention.

In the first place, a great number of recombinant plasmids in which to a plasmid vector are attached a plurality of DNA fragments including a DNA fragment containing the objective gene are prepared. The recombinant plasmids can be obtained by any known method in the biological field.

The recombinant plasmids are introduced into bacteria such as *Escherichia coli* through infection. A nitrocellulose filter is placed on a selective agar plate which allows only cells containing plasmid to grow. The cells are then spread on the filter to form colonies (FIGS. 1-(a), 1a colony, 2a agar plate). The resulting plate is hereinafter referred to as master plate. In the case that an agar plate of 9 cm in diameter is used, the number of the cells of *E. coli* preferably is $10^2$ to $10^3$ of cells per plate. The cells are grown until colonies reach approx. 1 to 2 mm in diameter.

A part of colonies are then transferred through printing from the agar plate having colonies formed thereon to a fresh filter, using a sterile velvet cloth. The relative locations of the resulting colonies on the filter agree completely with those of the colonies on the master plate.

Alternatively, a part of the colonies on the agar plate may be transferred to the fresh filter by gently placing the fresh filter on the agar plate and bringing the filter into contact with the plate in a short time. In this case, the relation between the locations of the resulting colonies on the filter and those of the colonies on the master plate is enantimorphous.

This operation is called replica or replica plating, and a part of each colony is blotted on the filter and thereby transferred thereonto without changing the locations of the colonies scattered over the agar plate. [FIGS. 1 (b), 1b: colony, 2b: filter]. Examples of the filters used for the replica plating include membrane filters composed of nitrocellulose, filter paper and the like.

In preparing this replica filter or before the preparation thereof, each of the master plate and filter is given with a mark so that the corresponding positions can be aligned with each other in the later step. [FIGS. 1, 3a, 3b: marks given with a drawing ink].

The cells on the filter are lysed by the conventional method and the exposed plasmid DNA is denatured by an alkali treatment to form single-stranded DNA which is then heat-treated to fix on the filter.

Separately, a probe is prepared by radioactively labeling DNA or RNA which is complementary to DNA containing the objective gene. The probe can be prepared by labeling the terminal of DNA having a base sequence complementary to the objective DNA or RNA with a radioisotope such as $^{32}P$, etc. There is no limitation on the kind of the radioisotope employed as the radioactive label. Any other radioisotopic nucleus than $^{32}P$ can be employed, provided that the nucleus radiates radiation such as $\alpha$-rays, $\beta$-rays, $\gamma$-rays, proton beams, neutron beams or X-rays. Examples of the employable radioisotope include $^{14}C$, $^{35}S$, $^{3}H$ and $^{125}I$ in addition to $^{32}P$.

Alternatively, the probe can be prepared by a nick translation method wherein one strand of unlabeled double-stranded DNA having the same base sequence as that of the objective DNA is nicked by endonuclease, and each nucleotide is removed sequentially from the nicked position on one strand and at the same time a radioactively labeled nucleotide is introduced thereinto, using DNA polymerase I. According to this method, a probe having high specific radioactivity can be obtained.

The above radioactively labeled probe is then hybridized with the denatured DNA on the filter by heat treatment. A container containing the radioactively labeled probe and the filter is warmed to denature DNA to single-stranded DNA and subsequently cooled to renature the DNA to double-stranded DNA or to form DNA-RNA hybrid. Since the recombinant DNA on the filter is fixed, only the recombinant DNA complementary to the DNA probe or RNA probe is hybridized to capture the radioactively labeled probe. Thus, only the recombinant DNA containing the objective gene forms a hybrid with the radioactively labeled DNA or RNA and hence, radioactive label is imparted thereto.

It is desirable that a mark is given on the filter with an ink containing a radioactive substance so that the corresponding locational relationship between the filter and the resulting autoradiograph can be identified. [FIG. 1-(c), 1c: hybridized colony, 2c: filter 3c: mark given with a drawing ink and additionally with a radiographic ink, 4c unhybridized colony, 1c and 4c are not distinguishable visually].

In forming the DNA-DNA hybrid by hybridization, it is desirable to mask the filter with one or some of various polymer solutions as a pretreatment for hybridization in order to prevent appearance of noise in the autoradiographic process caused by nonspecific adsorption of single-stranded DNA probe on the filter.

The filter on which the radioactively labeled substance is captured by the hybrid formation is then autoradiographed to identify the colony containing the objective gene.

The characteristic feature of the present invention resides in the autoradiographic process for obtaining the locational information of the two-dimensionally distributed objective genes. The autoradiographic process for obtaining such locational information is conducted in such a manner that exposure operation is carried out by placing the filter and the stimulable phosphor sheet together in layers for a given period of time to cause said phosphor sheet to absorb at least a portion of a radiation radiated by the radioactively labeled substance on the filter.

Usually, the filter is placed in close contact with the stimulable phosphor sheet during the exposure operation, but it is not always required to place the filter in close contact with the stimulable phosphor sheet and they may be placed adjacent to each other. The filter is not always required in a dry state, may be in a wet state and may be wrapped in a polyethylene sheet, etc., having a thickness which does not interfere with a radiation from the probe.

The exposure time varies depending on the radiation intensity of the radioactively labeled substance attached to in the filter, the amount of said substance, the sensitivity of the stimulable phospor sheet and the distance between the filter and the stimulable phosphor sheet, but the exposure operation must be carried out for a certain period of time, for example, for at least several seconds. When the stimulable phosphor sheet of the present invention is used as a radiosensitive material, however, the exposure time can be greatly shortened as compared with that required for the case where the conventional radiographic film is used. In the operation for reading out the locational information of the radioactively labeled substance on the filter, said information being transferred and stored from the filter to the stimulable phosphor sheet by exposure, the precise control of the exposure time in the exposure operation is not always required, since the resulting locational information can be suitably processed through applying various electrical processing thereto according to the intensity and distribution of energy stored in the phosphor sheet and the desired information, for example, by setting the amplification of the resulting electric signal to a given value.

There is no specific limitation on the temperature for carrying out the exposure operation and it is possible to carry out the exposure at an ambient temperature within the range of from 10° to 35° C. in the autoradiographic process utilizing the stimulable phosphor sheet of the present invention. If desired, the exposure operation may be, of course, carried out at a low temperature of approx. 5° C. or lower as in the conventional autoradiography.

The stimulable phosphor sheet suitably employable in the aforementioned autoradiography is composed basically of a support and a phosphor layer comprising a binder and a stimulable phosphor dispersed therein, the phosphor layer being provided on said support. However, in the case that the phosphor layer is of a self-supporting type, the support is not always required.

The stimulable phosphor sheet having the above-described constituents can be prepared, for instance, by the following procedure.

In the first place, phosphor particles and a binder are added to an appropriate solvent (e.g., a lower alcohol, chlorine atom-containing hydrocarbon, ketone, ester, ether), and then they are well mixed to prepare a coating dispersion of the phosphor particles in the binder solution.

Examples of the binder include proteins such as gelatin and synthetic polymers such as polyvinyl acetate, nitrocellulose, polyurethane, polyvinyl alcohol and linear polyester.

The ratio between the binder and the phosphor in the coating dispersion generally is within the range of from 1:8 to 1:40 (binder:phosphor, by weight).

The coating dispersion is then coated evenly on a support to form a coating layer, and the coating layer gradually heated to dryness to prepare the phosphor layer on the support. The thickness of the phosphor layer generally ranges from 50 to 500 $\mu$m.

The support may be any one of supports made of various materials which have been known as supports of intensifying papers (i.e., intensifying screens) in the conventional radiography. Examples of the employable supports include films of plastic materials such as cellulose acetate and polyethylene terephthalate, metallic sheets such as aluminum foil, ordinary papers, baryta papers, and resin-coated papers.

On the surface of the support to receive the phosphor layer may be provided one or more of an adhesive layer, a light-reflecting layer, a light-absorbing layer, etc.

On the surface of the phosphor layer opposite to the surface to face the support, a transparent protective film may be provided to protect the phosphor layer from physical and chemical deterioration. Examples of the material of the protective film include cellulose acetate, polymethyl methacrylate, polyethylene terephthalate and polyethylene. The thickness of the transparent protective film generally ranges from 0.1 to 20 $\mu$m.

Moreover, the surface of the stimulable phosphor sheet may be treated, for instance, hydrophilically, if desired.

The stimulable phosphor contained in the stimulable phosphor sheet utilized in the present invention gives stimulated emission when excited with stimulating rays after exposure to a radiation. From the viewpoint of practical use, the stimulable phosphor is desired to give stimulated emission in the wavelength region of 300–500 nm when excited with stimulating rays in the wavelength region of 400–850 nm.

Examples of the stimulable phosphor employable in the radiation image storage panel of the present invention include:

SrS:Ce,Sm, SrS:Eu,Sm, ThO$_2$:Er, and La$_2$O$_2$S Eu,Sm, as described in U.S. Pat. No. 3,859,527;

ZnS:Cu,Pb, BaO.xAl$_2$O$_3$:Eu, in which x is a number satisfying the condition of $0.8 \leq x \leq 10$, and $M^{2+}$O.xSiO$_2$:A, in which $M^{2+}$ is at least one divalent metal selected from the group consisting of Mg, Ca, Sr, Zn, Cd and Ba, A is at least one element selected from the group consisting of Ce, Tb, Eu, Tm, Pb, Tl, Bi and Mn, and x is a number satisfying the condition of $0.5 \leq x < 2.5$, as described in U.S. Pat. No. 4,326,078;

(Ba$_{1-x-y}$,Mg$_x$,Ca$_y$)FX:aEu$^{2+}$, in which one element selected from the group consisting of Cl and Br, x and y are numbers satisfying the conditions of $0 < x+y \leq =0.6$, and $xy \neq 0$, and a is a number satisfying the condition of $10^{-6} \leq a \leq 5 \times 10^{-2}$, as Patent Provisional Publication No. 55(1980)-12143;

LnOX:xA, in which Ln is at least one element selected from the group consisting of La, Y, Gd and Lu, X is at least one element selected from the group consisting of Cl and Br, A is at least one element selected from the group consisting of Ce and Tb, and x is a number satisfying the condition of $0 < x < 0.1$, as described in the above-mentioned U.S. Pat. No. 4,236,078;

(Ba$_{1-x}$,M$^{II}_x$)FX:yA, in which M$^{II}$ is at least one divalent metal selected from the group consisting of Mg, Ca, Sr, Zn and Cd, X is at least one element selected from the group consisting of Cl, Br and I, A is at least one element selected from the group consisting of Eu, Tb, Ce, Tm, Dy, Pr, Ho, Nd, Yb and Er, and x and y are numbers satisfying the conditions of $0 \leq x \leq 0.06$ and $0 \leq y \leq 0.2$, respectively, as described in Japanese Patent Provisional Publication No. 55(1980)-12145;

M$^{II}$FX.xA:yLn, in which M$^{II}$ is at least one element selected from the group consisting of Ba, Ca, Sr, Mg, Zn and Cd; A is at least one compound selected from the group consisting of BeO, MgO, CaO, SrO, BaO, ZnO, Al$_2$O$_3$, Y$_2$O$_2$, La$_2$O$_3$, In$_2$O$_3$, SiO$_2$, TiO$_2$, ZrO$_2$, GeO$_2$, SnO$_2$, Nb$_2$O$_5$, Ta$_2$O$_5$ and ThO$_2$; Ln is at least one element selected from the group consisting of Eu, Tb, Ce, Tm, Dy, Pr, Ho, Nd, Yb, Er, Sm and Gd; X is at least one element selected from the group consisting of Cl, Br and I; and x and y are numbers satisfying the conditions of $5 \times 10^{-5} \leqq x \leqq 0.5$ and $0 < y \leqq 0.2$, respectively, as described in Japanese Patent Provisional Publication No. 55(1980)-160078;

$(Ba_{1-x}, M^{II}_x)F_2.aBaX_2:yEu,zA$, in which $M^{II}$ is at least one element selected from the group consisting of Be, Mg, Ca, Sr, Zn and Cd; X is at least one element selected from the group consisting of Cl, Br and I; A is at least one element selected from the group consisting of Zr and Sc; and a, x, y and z are numbers satisfying the conditions of $0.5 \leqq a \leqq = 1.25$, $0 \leqq x \leqq 1$, $10^{-6} \leqq y \leqq 2 \times 10^{-1}$, and $0 < z \leqq 10^{-2}$, respectively, as described in Japanese Patent Provisional Publication No. 56(1981)-116777;

$(Ba_{1-x}, M^{II}_x)F_2.aBaX_2:yEu,zB$, in which $M^{II}$ is at least one element selected from the group consisting of Be, Mg, Ca, Sr, Zn and Cd; X is at least one element selected from the group consisting of Cl, Br and I; and a, x, y and z are numbers satisfying the conditions of $0.05 \leqq a \leqq 1.25$, $0 \leqq x \leqq 1$, $10^{-6} \leqq y \leqq 2 \times 10^{-1}$, and $0 < z \leqq 2 \times 10^{-1}$, respectively as described in Japanese Patent Provisional Publication No. 57(1982)-23673;

$(Ba_{1-x}, M^{II}_x)F_2.aBaX_2:yEu,zA$, in which $M^{II}$ is at least one element selected from the group consisting of Be, Mg, Ca, Sr, Zn and Cd; X is at least one element selected from the group consisting of Cl, Br and I; A is at least one element selected from the group consisting of As and Si; and a, x, y and z are numbers satisfying the conditions of $0.5 \leqq a \leqq 1.25$, $0 \leqq x \leqq 1$, $10^{-6} \leqq y \leqq 2 \times 10^{-1}$, and $0 < z \leqq 5 \times 10^{-1}$, respectively, as described in Japanese Patent Provisional Publication No. 57(1982)-23675;

$M^{III}OX:xCe$, in which $M^{III}$ is at least one trivalent metal selected from the group consisting of Pr, Nd, Pm, Sm, Eu, Tb, Dy, Ho, Er, Tm, Yb, and Bi; X is at least one element selected from the group consisting of Cl and Br; and x is a number satisfying the condition of $0 < x < 0.1$, as described in Japanese Patent Provisional Publication No. 58(1983)-69281;

$Ba_{1-x}M_{x/2}L_{x/2}FX:yEu^{2+}$, in which M is at least one alkali metal selected from the group consisting of Li, Na, K, Rb and Cs; L is at least one trivalent metal selected from the group consisting of Sc, Y, La, Ce, Pr, Nd, Pm, Sm, Gd, Tb, Dy, Ho, Er, Tm, Yb, Lu, Al, Ga, In and Tl; X is at least one halogen selected from the group consisting of Cl, Br and I; and x and y are numbers satisfying the conditions of $10^{-2} \leqq x \leqq 0.5$ and $0 < y \leqq 0.1$, respectively, as described in Japanese Patent Provisional Publication No. 58(1983)-206678;

$BaFX.xA:yEu^{2+}$, in which X is at least one halogen selected from the group consisting of Cl, Br and I; A is at least one fired product of a tetrafluoroboric acid compound; and x and y are numbers satisfying the conditions of $10^{-6} \leqq x \leqq 0.1$ and $0 < y \leqq 0.1$, respectively, as described in Japanese Patent Provisional Publication No. 59(1984)-27980;

$BaFX.xA:yEu^{2+}$, in which X is at least one halogen selected from the group consisting of Cl, Br and I; A is at least one fired product of a hexafluoro compound selected from the group consisting of monovalent and divalent metal salts of hexafluoro silicic acid, hexafluoro titanic acid and hexafluoro zirconic acid; and x and y are numbers satisfying the conditions of $10^{-6} \leqq x \leqq 0.1$ and $0 < y \leqq 0.1$, respectively, as described in Japanese Patent Provisional Publication No. 59(1984)-47289;

$BaFX.xNaX':aEu^{2+}$, in which each of X and X' is at least one halogen selected from the group consisting of Cl, Br and I; and x and a are numbers satisfying the conditions of $0 < x \leqq 2$ and $0 < a \leqq 0.2$, respectively, as described in Japanese Patent Provisional Publication No. 59(1984)-56479;

$M^{II}FX.xNaX':yEu^{2+}:zA$, in which $M^{II}$ is at least one alkaline earth metal selected from the group consisting of Ba, Sr and Ca; each of X and X' is at least one halogen selected from the group consisting of Cl, Br and I; A is at least one transition metal selected from the group consisting of V, Cr, Mn, Fe, Co and Ni; and x, y and z are numbers satisfying the conditions of $0 < x \leqq 2$, $0 < y \leqq 0.2$ and $0 < z \leqq 10^{-2}$, respectively, as described in Japanese Patent Provisional Publication No. 59(1984)-56480; and $M^{II}FX.aM^{I}X'.bM'^{II}X''_2cM^{III}X'''_3.xA:yEu^{2-}$, in which $M^{II}$ is at least one alkaline earth metal selected from the group consisting of Ba, Sr and Ca; $M^{I}$ is at least one alkali metal selected from the group consisting of Li, Na, K, Rb and Cs; $M'^{II}$ is at least one divalent metal selected from the group consisting of Be and Mg; $M^{III}$ is at least one trivalent metal selected from the group consisting of Al, Ga, In and Tl; A is at least one metal oxide; X is at least one halogen selected from the group consisting of cl, Br and I; each of X', X'' and X''' is at least one halogen selected from the group consisting of F, Cl, Br and I; a, b and c are numbers satisfying the conditions of $0 \leqq a \leqq 2$, $0 \leqq b \leqq 10^{-2}$, $0 \leqq c \leqq 10^{-2}$ and $a + b + c \leqq 10^{-6}$; and x and y are numbers satisfying the conditions of $0 < x \leqq 0.5$ and $0 < y \leqq 0.2$, respectively, as described in Japanese Patent Application No. 57(1982)-184455.

The above-described stimulable phosphors are given by no means to restrict the stimulable phosphor employable in the present invention. Any other phosphor can be also employed, provided that the phosphor gives stimulated emission when excited with stimulating rays after exposure to a radiation.

Detailed description on the stimulable phosphor sheet and the exposing procedure employable in the present invention is given in Japanese Patent Application No. 57(1982)-193418 (U.S. patent application Ser. No. 549,417 and European Patent Application No. 83 110 984.8).

A method for reading out or detecting the information on the dimensional location of the radioactively labeled substances stored in the stimulable phosphor sheet will be described below briefly, referring to an embodiment of a read-out system shown in FIG. 2 of the accompanying drawings.

Figure 2:
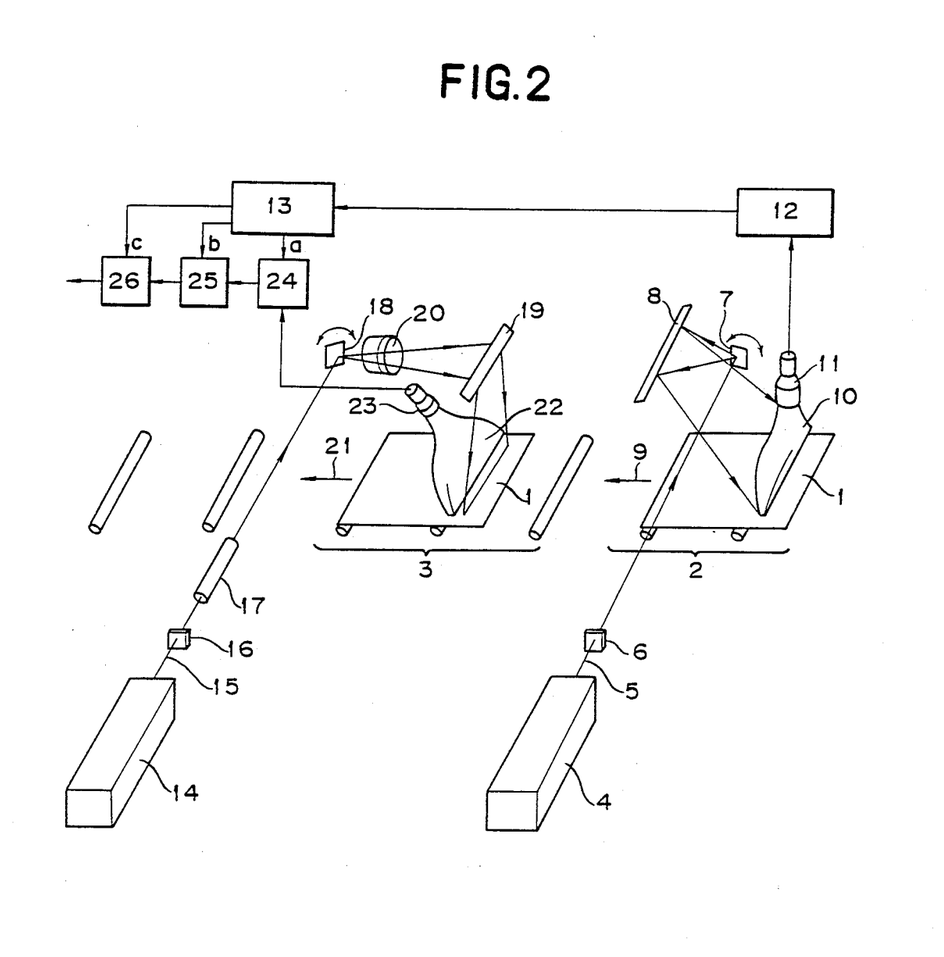
FIG. 2 schematically illustrates an embodiment of the read-out device for reading out the locational information on the radioactively labeled substance on a filter, which is recorded and stored on the stimulable phosphor sheet according to the present invention.

FIG. 2 schematically illustrates an embodiment of the read-out system comprising a preliminary read-out section 2 for preliminarily reading out the two dimensional information on the location of the radioactively labeled substances stored (or recorded) in the stimulable phosphor sheet 1 (stimulable phosphor sheet may be hereinafter referred to as "phosphor sheet"), and a final read-out section 3 for finally reading out the desired locational information on the radioactively labeled substance stored in the phosphor sheet 1.

In the preliminary read-out section 2, the preliminary read-out operation is carried out in the following manner.

Laser beam 5 generated by a laser source 4 first passes through a filter 6 to cut off a light beam in the wavelength region corresponding to the wavelength region of stimulated emission to be emitted from the phosphor sheet 1 in response to stimulation with the laser beam 5. The laser beam 5 is subsequently deflected by a beam deflecter 7 such as a galvanometer mirror, and reflected by a plane reflecting mirror 8. The deflected beam then impinges upon the phosphor sheet 1. The laser source 4 used herein is so selected as to avoid overlapping of the wavelength region of the laser beam 5 with the main wavelength region of the stimulated emission to be emitted from the phosphor sheet 1.

The phosphor sheet 1 is transferred in the direction along the arrow 9 under the irradiation of the above-mentioned deflected laser beam. Therefore, the whole surface of the phosphor sheet 1 is subjected to the irradiation of the deflected laser beam. The power of the laser beam 5 employed in the preliminary read-out section is adjusted to be lower than the power of the laser beam to be employed in the final read-out section by controlling the output of the laser source 4, the beam diameter of the laser beam 5, the scanning speed of the laser beam 5, and the transferring speed of the phosphor sheet 1.

When irradiated with the above-mentioned laser beam, the phosphor sheet 1 gives stimulated emission having the emission intensity proportional to the radiation energy stored (or recorded) therein. The emission then enters into a light guiding sheet 10 for the preliminary read-out. The light guiding sheet 10 has a linear edge face for receiving the emission, and the edge face is so positioned in the vicinity of the phosphor sheet as to correspond to the scanning line on the phosphor sheet 1. The exit of the light guiding sheet 10 is in the form of a ring and is connected to an light-receiving face of a light detector 11 is such as a photomultiplier. The light guiding sheet 10 is made, for instance, by processing a sheet of a transparent thermoplastic resin such as a polyacrylic synthetic resin, and so constituted that the emission introduced from the linear edge face is transmitted to the exit under repeated total reflection within the sheet 10. The stimulated emission from the phosphor sheet 1 is guided in the interior of the light guiding sheet 10 to the exit, and received by the light detector 11.

On the light-receiving face of the light detector 11 is provided a filter which allows only the light of wavelength region of the stimulated emission to pass through and cuts off the light of the wavelength region of the stimulating rays (laser beam) so as to detect only the stimulated emission. The stimulated emission detected by the light detector 11 is converted to an electric signal, amplified in an amplifier 12 and transmitted to the output. The stored information output from the amplifier 12 is supplied to a control circuit 13 of the final read-out section 3. The control circuit 13 provides an amplification degree setting value a, a scale factor setting value b, and an image processing condition setting value c, for obtaining a well readable image having uniform concentration and contrast regardless of variation of the detected information.

The phosphor sheet 1 having been subjected to the preliminary read-out in the above-described manner is then transferred to the final read-out section 3.

In the final read-out section 3, the following read-out operation is performed.

The laser beam 15 generated by a laser source 14 for the final read-out passes through a filter 16 having the same function as that of the above-mentioned filter 6, and then the beam diameter is precisely adjusted in a beam expander 17. Subsequently, the laser beam is deflected by a beam deflector 18 such as a galvanometer mirror, and reflected by a plane reflection mirror 19.

The deflected beam then impinges one-dimensionally upon the phosphor sheet 1. Between the beam deflector 18 and the plane reflection mirror 19 a $f\theta$ lens 20 is provided so that the beam speed is continuously kept constant while the deflected laser beam scans the phosphor sheet 1.

The phosphor sheet 1 is transferred in the direction along the arrow 21 under the irradiation with the above-mentioned deflected laser beam. Accordingly, the whole surface of the phosphor sheet is subjected to the irradiation in the same manner as in the preliminary read-out operation.

When irradiated with the above-mentioned laser beam, the phosphor sheet 1 gives the stimulated emission in proportion to the radiation energy stored therein in the same manner as in the preliminary read-out operation. The emission then enters into a light guiding sheet 22 for the final read-out. The light guiding sheet 22 for the final read-out is made of the same material and has the same constitution as the light guiding sheet 10 employed for the preliminary read-out. The stimulated emission received is guided in the interior of the light guiding sheet 22 up to the exit under repeated total reflection, and then received by a light detector 23. On the light-receiving face of the light detector 23 is provided a filter which allows only the light of wavelength region of the stimulated emission to pass through and cuts off the light of the wavelength region of the stimulating rays (laser beam) so as to detect only the stimulated emission.

The stimulated emission detected by the light detector 23 is converted to an electric signal, amplified to an electric signal adjusted to an appropriate level in an amplifier 24 acccording to the aforementioned amplification degree setting value a and transmitted to an A/D converter 25. The adjusted electric signal is then converted to a digital signal in the A/D converter 25 according to an appropriate scale factor defined by the scale factor setting value b, and then the digital signal is input into a signal processing circuit 26. In the signal processing circuit 26, the digital signal is processed according to the image processing condition setting value c for obtaining a well readable visible image having appropriate density and contrast regardless of variation of the detected information. If desired, the signal thus processed is then transmitted to a recording device (not shown) via a data preserving means such as a magnetic tape.

Various recording devices based on various systems can be employed for the above described purpose, for instance, a device for visualizing optically by scanning a photosensitive material with laser beam, etc., a display means for visualizing electrically on CRT, etc., a means for printing a radiation image displayed on CRT by means of video printer, and a means for visualizing on heat-sensitive recording material using thermic rays.

The recording device used in the present invention is not restricted to the visualizing devices such as mentioned above, and the two dimensional information on the location of the radioactively labeled substance can be recorded, for example, in the form of numerals and-/or symbols.

In the above description on the method for reading out the locational information on the radioactively labeled substances stored in the stimulable phosphor sheet, a read-out operation involving both the preliminary read-out operation and the final read-out operation has been given. However, the read-out operation employable in the present invention is not limited to the above-described embodiment. For instance, the preliminary read-out operation may be omitted if the content of the radioactive substances on the filter and an adequate exposure time for the filter is previously known.

Further, other suitable methods than the above-mentioned embodiments may be used for reading out the locational information of the radioactively labeled substances stored in the stimulable phosphor sheet.

The objective gene on the filter can be identified from the thus obtained two dimensional information on the location of the radioactively labeled substance.

For example, in the case that the autoradiograph of the filter is obtained as a visual image using a radiographic film, only positions corresponding to colonies containing the objective gene are detected as black spots. Hence, when the radiographic film is put upon the filter in such a manner that marks previously put agree with each other, the objective gene on the filter can be identified. [FIGS. 1-(d), 1d: black spot, 2d radiographic film, and 3d: mark blackened by radiographic ink]

The master plate is put upon the radiographic film having the visualized autoradiograph so as to make the marks agree with each other, the colonies on the filter, which agree with the black spots on the radiographic film are visually identified, and the colonies containing the objective gene are deteted and collected. However, even though the visualized autoradiograph on the radiographic film has the same size as that of nitrocellulose filter, the filter is shrunk in the course of the hybridization treatment so that care should be taken that the size of the resulting autoradiograph is somewhat smaller than that of the master plate.

The autoradiographic method of the present invention for identifying the colony which comprises obtaining the two dimensional information on the location of the objective gene present on the filter is not limited to the above-described method which comprises visually identifying the locational information by putting the filter and/or the master plate upon the visualized autoradiograph on the radiographic film. For example, it is possible to identify the colony present at a location corresponding to the digital value of the resulting numerals and/or symbols by expressing the locational information with the numerals and/or symbols.

The screening of the genes is usually performed by repeatedly carrying out the screening procedure several times in the case that a DNA fragment corresponding to one gene is selectively picked out of the genome DNA, and the screening operation of the present invention can be also carried out repeatedly.

While the gene-screening method using colony hybridization has been described in the above, other methods than the colony hybridization, such as plaque hybridization can be also used in the present invention.

This plaque hybridization method is one which uses phage (virus which invades bacteria through infection and lyses the cells to grow itself) as a vector in performing the DNA recombination of DNA fragments containing the objective gene. In this method, said DNA fragment is recombined with a DNA contained in the phage to form recombinant phage, and the resulting recombinant phage is placed on an agar plate culture medium containing bacteria as host, for example, on a plate having the lawn of the cells of *E. coli* on the upper part of the agar medium, whereby the recombinant phage invades the host *E. coli* through infection and grows itself, and then plaques are formed on the agar plate.

The gene-screening method of the present invention can be carried out in such a manner that the agar plate carrying plaques formed thereon is used as master plate, a replica filter is prepared from the above plate using a filter such as nitrocellulose filter, the objective DNA is hybridized with a radioactively labeled probe in a similar manner to that described above, the hybridized mixture is autoradiographed, the objective gene on the filter is identified according to the resulting two dimensional information on the location of the objective gene, and the plaques containing the objective gene are detected and isolated from the master plate.

The plaque hybridization method is capable of screening about $10^4$ recombinant phages per one screening operation (using a plate of about 15 cm in diameter). Accordingly, the plaque hybridization is more efficient than the colony hybridization and hence, enables genes to be screened simply and rapidly. In the case that "in vitro packaging method" is used in the formation of recombinant gene, the recombinant phage can be obtained at a high efficiency. Further, this method is suitable for handling a large amount of clones from the viewpoint of stability of phage. Thus, the plaque hybridization method has many advantages.

The following examples illustrate the embodiments of the present invention. The stimulable phosphor sheet used in the following examples was prepared in the following manner.

Methyl ethyl ketone was added to a mixture of stimulable phosphor particles (particles of divalent europium activated barium fluorobromide phosphor, BaFBr:Eu$^{2+}$) and a linear polyester resin. Nitrocellulose (nitrification degree: 11.5%) was then added thereto to prepare a dispersion containing the phosphor particles dispersed therein. Tricresyl phosphate, n-butanol and methyl ethyl ketone were then added to the dispersion. The resulting mixture was thoroughly stirred by means of a propeller mixer to prepare a coating dispersion having a viscosity of 25 to 25 PS at 25° C., in which the phosphor particles were uniformly dispersed and the mixing ratio of the binder to the phosphor was 1:25 by weight.

The coating dispersion was uniformly coated on the surface of a carbon black-containing polyethylene terephthalate sheet (support, 250 μm in thickness) placed horizontally on a glass plate by using a doctor blade. After the coating was complete, the support having a coating film formed thereon was placed in a dryer and the temperature within the dryer was gradually elevated from 25° C. to 100° C. to dry the coating film, thus forming a phosphor layer of 300 μm in thickness on the support.

A polyester adhesive was applied to one side of a transparent polyethylene terephthalate film (12 μm in thickness), and the film was then bonded to the surface of the phosphor layer by placing the film in such a manner that the adhesive layer faces the phosphor layer to form a protective film thereon. Thus, the stimulable phosphor sheet consisting of the support, the phosphor layer and the protective film was prepared.

EXAMPLE 1

(1) Formation of colony and preparation on replica filter

Two nitrocellulose filters (9 cm in diameter; HAWP 90, manufactured by Millipore Corporation) were combined in layers, and marks were put thereon at three points by puncturing the filter with a hypodermic needle containing a drawing ink. One of them was placed on an L-agar culture medium (1% Bacto-tryptone, 0.5% yeast extract and 0.5% NaCl, pH 7.0 to 7.1) in a petri dish and *Escherichia coli* HB 101 strain (pBR 322-retaining cells and non-retaining cells were mixed in a ratio of 1:100) was spread over the filter in a rate of about $5 \times 10^3$ cells per plate. The filter plate was incubated at 37° C. for about 10 hours to form colonies which were about 1 mm in diameter. This plate is hereinafter referred to as master plate.

A part of the colonies on the master plate was transferred to another nitrocellulose filter with a sterile velvet cloth in such a manner that the marks of the drawing ink were made to correspond with each other. The resulting filter is hereinafter referred to as replica filter. This replica filter was placed on a fresh L-agar culture medium and incubated at 37° C. for about 5 hours to allow colonies to grow until they reached about 1 mm in 15 diameter. The master plate was preserved at a temperature of 4° C.

(2) Hybridization treatment

The replica filter was gently peeled off from the medium, treated with an aqueous solution of 0.5N aqueous sodium hydroxide to lyse the colonies and to denature the recombinant DNA to single-stranded DNA, and then neutralized with a 0.5M Tris-HCl buffer solution (pH 8). The filter was washed with an aqueous solution of 0.3M sodium chloride and treated at 80° C. in vacuo for two hours to fix on the filter the recombinant DNA. This filter was soaked in a 5-fold concentrated Denhardt solution (1×Denhardt solution: a solution containing 0.02% bovine serum albumin, 0.02% polyvinyl pyrrolidone and 0.02% Ficoll) kept at 68° C. for 3 hours.

A pBR 322 probe (specific activity: $1 \times 10^6$ cpm/$\mu$g) radioactively labeled by nick translation method was dissolved in a solution containing Denhardt solution, 0.75M sodium chloride, 0.15M Tris-HCl buffer solution (pH 8), 5 mM EDTA and 0.1% SDS (sodium dodecyl-sulfate) to prepare a hybridization solution. The above filter was introduced into this solution and incubated at 68° C. for 16 hour to effect hybridization with the radioactively labeled probe on the filter. The concentration of the probe was adjusted so as to give a specific activity of about $1 \times 10^5$ cpm/filter. This filter was washed by repeating three times by soaking it in a solution containing 0.3 mM sodium chloride, 60 mM Tris-HCl buffer solution (pH 8), 2 mM EDTA and 0.5% SDS kept at 68° C. Further. the filter was washed by soaking it in 3M Tris-solution at room temperature for four hours, transferred onto a filter paper and dried at room temperature.

The resulting replica filter was sticked on Whatman paper, and a droplet of a dye solution of Bromphenol Blue (BPB) containing a small amount of $^{32}P$-rATP (hereinafter referred to as radiographic ink) was allowed to drop onto the mark previously put with the drawing ink.

(3) Identification of gene by autoradiographic process and collection of the same.

The filter paper having the replica filter sticked thereon and the stimulable phosphor sheet were placed in layers, introduced into a cassette and kept for exposure at room temperature for three hours. The stimulable phosphor sheet was then placed in the read-out device of FIG. 2 to read out the autoradioautograph of the replica filter which was stored in the stimulable phosphor sheet, whereby the two dimensional information on the location of the radioactively labeled probe was obtained as digital values.

According to the resulting digital information, a photographic film was exposed by using a laser scanning device and developed to obtain the autoradiograph having a visualized image. The visualized image had an image quality comparable with that of the image obtained through the procedure of Comparison Example 1. The film and the master plate were combined together in such a manner that the radiographic ink position of the film was made to correspond with the mark on the master plate previously put with the drawing ink, whereby the colonies in regions corresponding to the black spots on the film were easily identified.

The digital information on the location of the radioactively labeled hybrid was displayed on CRT to obtain an image corresponding to the above autoradiograph. The master plate was placed on the CRT in such a manner that relative positions were made to agree with each other, whereby colonies corresponding to bright spots (showing the location of the radioactively labeled probes) displayed on CRT were picked up from the master plate. This operation for picking up colonies containing the objective DNA was readily carried out.

For the purpose of confirmation, another replica filter was prepared from the master plate, from which the colonies containing the objective DNA had been removed. This replica filter was subjected to a hybridizaton treatment in a similar manner to that described above and dried. The procedure for obtaining the autoradiograph of the filter was conducted using the stimulable phosphor sheet, and it was confirmed that there remained no colonies being hybridizable with the radioactively labeled probe.

Thus, it has been confirmed that the autoradiography using the stimulable phosphor sheet makes it possible to give the two dimensional information on the location of the radioactively labeled probe by a short-time exposure operation at room temperature. It has been also confirmed that *E. coli* containing recombinant plasmids contain ing the objective DNA can be efficiently screened completely in a short time by the above-described screening method.

COMPARISON EXAMPLE 1

In the procedure of Example 1-(3) for the autoradiographic identification and collection of the gene, a medical radiographic film (RX: manufactured by Fuji Photo Film Co., Ltd.) in combination with a fluorescent intensifying screen (High standard 3D: manufactured by Fuji Photo Film Co., Ltd.) were used in place of the stimulable phosphor sheet. A filter paper having a replica filter sticked thereon, the radiographic film and the intensifying screen were combined together, placed in a medical radiographic cassette for direct photographic process to expose the film at a temperature of −80° C. for 70 hours in a dark room. The radiographic film was developed, fixed, washed with water and dried to obtain the visible autoradiograph of the hybridized radioactively labeled probes.

The resulting image had an image quality corresponding to that of the autoradiograph obtained in the form of a visualized image on the photographic film in Example 1.

It is apparent from Example 1 and Comparative Example 1 that the gene-screening method of the present invention (Example 1) allows the objective gene to be screened and isolated in a short time by a simple procedure as compared with the conventional screening method (Comparative Example 1). It is also found that the objective gene can be screened efficiently in a high purity according to the present invention.

EXAMPLE 2

(1) Formation of plaque and preparation of replica filter

DNA of cultured rat cell transformed by EcoC fragments of human adenovirus 12 type (Ad-12) DNA was partially cleaved with EcoRI to obtain a gene library inserted into cloning vector Charon 4A. The library was introduced into cells of *E. coli* through infection in a conventional manner, mixed with an agar solution, spread in a rate of about $10^4$ per plate over a plate (9 cm in diameter) having L-agar medium placed thereon, and incubated at 37° C. for about 15 hours to form plaques.

A nitrocellulose filter (HAWP 90, manufactured by Millipore Corporation) was gently placed on the culture medium containing the formed plaques so that a part of the plaques was transferred onto the filter by a conventional method. The resulting filter is hereinafter referred to as replica filter. The filter and the plate were previously marked by puncturing them with a hypodermic needle containing a drawing ink in a position in such a manner that the face and the back of the filter were distinguishable from each other. The above plate was identified as master plate and preserved at 4° C.

(2) Hybridization treatment

The procedure of Example 1 was repeated except that Ad-12 Hind-IIIG fragment radioactively labeled by nick translation (specific activity : $1 \times 10^7$ cpm/$\mu$g) was used as the radioactively labeled probe and the concentration of the probe was adjusted so as to give a specific activity of about $2 \times 10^5$ cpm per filter to perform hybridization of the filter.

(3) Autoradiographic identification and collection of gene

The procedure of Example 1 using the stimulable phosphor sheet was repeated except that the exposure time was changed to 4 hours to obtain autoradiograph having the two dimensional information on the location of the radioactively labeled probe as digital value.

The subsequent treatment was carried out according to the resulting digital information in a similar manner to that described in Example 1 using a laser scanning device to obtain the autoradiograph having a visualized image on the photographic film. The visualized image had an image quality comparable with that of an image obtained by the conventional autoradiography of Comparison Example 2. The film and the master plate were put together in such a manner that relative positions were made to correspond with each other, whereby the plaques containing the objective DNA were identified from the master plate.

The digital information was displayed on CRT to obtain an image corresponding to the above autoradiograph. The master plate was placed on the CRT in such a manner that relative positions were made to agree with each other, whereby plaques corresponding to the bright spots (showing location of the radioactively labeled probes) displayed on CRT were identified and picked up from the master plate. This operation for screening and picking up the plaques containing the objective DNA were easily carried out.

For the purpose of confirmation, a replica filter was prepared from the master plate, from which the plaques containing the objective DNA had been removed. The replica filter was subjected to a hybridization treatment in a similar manner to that described above and dried. The operation for obtaining the autoradiograph of the filter was conducted using the stimulable phosphor sheet, and it was confirmed that there remained no plaues hybridizable with the radioactively labeled probe.

It has been found that the autoradiography using the stimulable phosphor sheet makes it possible to give the two dimensional information on the location of the radioactively labeled probes by a short exposing period operation at room temperature. It has been also found that recombinant phage containing the objective DNA can be efficiently screened completely in a short time by the above-described screening method.

COMPARISON EXAMPLE 2

In the procedure of Example 2-(3) for autoradiographic identification and collection of the gene, a medical radiographic film (RX: manufactured by Fuji Photo Film Co., Ltd.) in combination with a fluorescent intensifying screen (High Standard 3D: manufactured by Fuji Photo Film Co., Ltd.) were used in place of the stimulable phosphor sheet. A filter paper having a replica filter sticked thereon, the radiographic film and the intensifying screen were combined together, placed in a medical radiographic cassette for a direct photographic process to expose the film at a temperature of $-80°$ C. for 80 hours in a dark room. The radiographic film was developed, fixed, washed with water and dried to obtain the autoradiograph of the hybridized radioactively labeled probe.

The resulting image had an image quality corresponding to that of the autoradiograph obtained as a visualized image on the photographic film given in Example 2.

It is apparent from Example 2 and Comparison Example 2 that the gene-screening method of the present invention (Example 2) allows the objective gene to be screened and collected in a short time by a simple operation as compared with the conventional screening method (Comparison Example 2). It has been also found that the objective gene can be screened efficiently in high purity according to the present invention.

We claim:
1. In an autoradiographic gene-screening method empolying a hybridization process comprising:
  (1) transferring a portion of clones cultured on a culture medium onto a filter and fixing the clones thereonto;
  (2) hybridizing the genes of said clones fixed onto said filter with radioactively labeled probes;
  (3) obtaining two-dimensional locational information of the resulting radioactively labeled genes on the filter which comprises placing said filter on a radiosensitive material to absorb at least a portion of radiation energy emitted by the radioactively labeled genes on the filter; and
  (4) recovering target clones of the culture medium according to the obtained two-dimensional locational information, the improvement comprising employing a stimulable phosphor sheet containing a stimulable phosphor as the radiosensitive material where the two-dimensional locational information of the radioactively labeled genes is obtained by exciting said stimulable phosphor with said radiation energy to release stimulated emission from said phosphor sheet, and detecting the stimulated emission, the improvement further comprising performing the procedure for placing the filter on the radiosensitive material at a temperature in the range of 10° of 35° C.

2. The autoradiographic gene-screening method as claimed in claim 1, wherein said gene-screening method is carried out by utilizing a colony hybridization process.

3. The autoradiographic gene-screening method as claimed in claim 1, wherein the gene-screening method is carried out by utilizing a plaque hybridization process.

4. The autoradiographic gene-screening method as claimed in any one of claims 1, 2, or 3, wherein said stimulation of the stimulable phosphor sheet with an electromagnetic wave in the step (3) is carried out by scanning said sheet with the electromagnetic wave.

5. The autoradiographic gene-screening method as claimed in any one of claims 1, 2, or 3, wherein said two dimensional information on the location of the radioactively labeled substances in the step (3) is obtained as an image.

6. The autoradiographic gene-screening method as claimed in any one of claims 1, 2, or 3, wherein said two dimensional information on the location of the radioactively labeled substances in the step (3) is expressed in the form of symbols and/or numerals.

7. The autoradiographic gene-screening method as claimed in any one of claims 1, 2, or 3, wherein said stimulable phosphor sheet comprises a support, a phosphor layer comprising a stimulable phosphor dispersed in a binder, and a protective layer.

8. The autoradiographic gene-screening method as claimed in claim 1, wherein the gene-screening method is carried out by repeating the steps (1) to (4).

* * * * *